US011006958B2

(12) United States Patent
Potter, Jr.

(10) Patent No.: US 11,006,958 B2
(45) Date of Patent: May 18, 2021

(54) DEVICES AND METHODS FOR ESOPHAGEAL LENGTHENING AND ANASTOMOSIS FORMATION

(71) Applicant: Mayo Foundation for Medical Education and Research, Rochester, MN (US)

(72) Inventor: D. Dean Potter, Jr., Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 111 days.

(21) Appl. No.: 16/382,711

(22) Filed: Apr. 12, 2019

(65) Prior Publication Data

US 2019/0239887 A1 Aug. 8, 2019

Related U.S. Application Data

(62) Division of application No. 15/493,947, filed on Apr. 21, 2017, now Pat. No. 10,299,795.

(Continued)

(51) Int. Cl.
*A61B 17/11* (2006.01)
*A61J 15/00* (2006.01)
(Continued)

(52) U.S. Cl.
CPC ........ *A61B 17/1114* (2013.01); *A61B 5/1076* (2013.01); *A61B 90/02* (2016.02); *A61J 15/0003* (2013.01); *A61J 15/0007* (2013.01); *A61J 15/0049* (2013.01); *A61B 2017/00876* (2013.01); *A61B 2017/1132* (2013.01); *A61B 2576/00* (2013.01)

(58) Field of Classification Search
CPC ........ A61B 17/11; A61B 17/1114–2017/1117; A61B 2017/1132; A61B 2018/00488; A61F 5/0003; A61F 5/003; A61F 5/0013; A61F 5/0079; A61J 15/0049
See application file for complete search history.

(56) References Cited

U.S. PATENT DOCUMENTS 4,134,405 A 1/1979 Smit
4,271,839 A 6/1981 Fogarty et al.
(Continued)

OTHER PUBLICATIONS

Foker et al., "A flexible approach to achieve a true primary repair of all infants with esophageal atresia," Semin Pediatr Surg., 14:8-15, Feb. 2005.

(Continued)

*Primary Examiner* — Darwin P Erezo
*Assistant Examiner* — Brigid K Byrd
(74) *Attorney, Agent, or Firm* — Fish & Richardson P.C.

(57) ABSTRACT

Devices and methods can be used to treat long gap esophageal atresia, while obviating much of the delay and complexities associated with current procedures. The devices and methods involve actively stretching the esophagus portions with traction to promote growth of the esophagus portions. Moreover, the devices and methods provided allow for a compression anastomosis to occur between the esophageal ends. This eliminates the need for a second operation to suture the esophageal ends together.

15 Claims, 6 Drawing Sheets

Related U.S. Application Data

(60) Provisional application No. 62/328,970, filed on Apr. 28, 2016.

(51) Int. Cl.
    *A61B 5/107*     (2006.01)
    *A61B 90/00*     (2016.01)
    *A61B 5/00*     (2006.01)
    *A61B 17/00*     (2006.01)

(56) References Cited

U.S. PATENT DOCUMENTS

| | | |
|---|---|---|
| 4,624,257 A | 11/1986 | Berggren et al. |
| 4,723,547 A | 2/1988 | Kullas et al. |
| 4,964,863 A | 10/1990 | Kanshin et al. |
| 5,092,839 A | 3/1992 | Kipperman |
| 5,141,516 A | 8/1992 | Detweiler |
| 5,282,827 A | 2/1994 | Kensey et al. |
| 5,312,410 A | 5/1994 | Miller et al. |
| 5,411,508 A | 5/1995 | Bessler et al. |
| 5,425,738 A * | 6/1995 | Gustafson ........... A61B 17/1114 606/151 |
| 5,447,503 A | 9/1995 | Miller |
| 5,486,196 A | 1/1996 | Hirshowitz et al. |
| 5,626,591 A | 5/1997 | Köckerling et al. |
| 5,868,760 A | 2/1999 | McGuckin, Jr. |
| 5,899,882 A | 5/1999 | Waksman et al. |
| 6,063,056 A | 5/2000 | Engelberg |
| 6,251,111 B1 | 6/2001 | Barker et al. |
| 6,689,062 B1 | 2/2004 | Mesallum |
| 6,743,244 B2 | 6/2004 | Blatter et al. |
| 6,869,437 B1 | 3/2005 | Hausen et al. |
| 7,220,268 B2 | 5/2007 | Blatter |
| 7,371,243 B1 | 5/2008 | Nielsen et al. |
| 7,527,590 B2 | 5/2009 | Suzuki et al. |
| 7,892,292 B2 | 2/2011 | Stack et al. |
| 8,083,758 B2 | 12/2011 | Hsu et al. |
| 8,480,694 B2 | 7/2013 | Heinrich et al. |
| 8,821,521 B2 | 9/2014 | Burnett |
| 9,414,878 B1 | 8/2016 | Wu et al. |
| 2001/0007931 A1 | 7/2001 | Blatter |
| 2002/0185517 A1 | 12/2002 | Vresh et al. |
| 2003/0216613 A1 * | 11/2003 | Suzuki .................... A61B 1/32 600/104 |
| 2003/0222117 A1 | 12/2003 | Orban, III |
| 2004/0097973 A1 * | 5/2004 | Loshakove ............ A61B 17/11 606/144 |
| 2004/0147801 A1 | 7/2004 | Kugler et al. |
| 2004/0153167 A1 | 8/2004 | Stack et al. |
| 2004/0215233 A1 | 10/2004 | Kaplan et al. |
| 2005/0021053 A1 | 1/2005 | Heinrich |
| 2005/0143766 A1 | 6/2005 | Bachmann et al. |
| 2005/0149071 A1 | 7/2005 | Abbott et al. |
| 2005/0149072 A1 | 7/2005 | DeVries et al. |
| 2005/0182475 A1 | 8/2005 | Jen et al. |
| 2005/0209614 A1 | 9/2005 | Fenter et al. |
| 2006/0079897 A1 * | 4/2006 | Harrison ............ A61B 17/7055 63/900 |
| 2006/0167474 A1 | 7/2006 | Bloom et al. |
| 2006/0253139 A1 | 11/2006 | Ortiz |
| 2006/0286145 A1 | 12/2006 | Horan et al. |
| 2007/0049954 A1 | 3/2007 | Caty et al. |
| 2007/0073098 A1 | 3/2007 | Lenker et al. |
| 2007/0265643 A1 | 11/2007 | Beane et al. |
| 2008/0015618 A1 | 1/2008 | Sonnenschein et al. |
| 2008/0172087 A1 | 7/2008 | Fuchs et al. |
| 2009/0018604 A1 | 1/2009 | Mitelberg et al. |
| 2009/0048618 A1 | 2/2009 | Harrison et al. |
| 2009/0281557 A1 * | 11/2009 | Sander .................. A61B 17/11 606/151 |
| 2010/0121371 A1 | 5/2010 | Brooks et al. |
| 2010/0179510 A1 | 7/2010 | Fox et al. |
| 2010/0222802 A1 | 9/2010 | Gillespie, Jr. et al. |
| 2011/0137325 A1 | 6/2011 | Nolan et al. |
| 2011/0218476 A1 | 9/2011 | Kraemer et al. |
| 2011/0264125 A1 | 10/2011 | Wilson et al. |
| 2011/0288570 A1 | 11/2011 | Copa |
| 2012/0024935 A1 | 2/2012 | Shelton, IV et al. |
| 2012/0035628 A1 | 2/2012 | Aguirre et al. |
| 2012/0204865 A1 | 8/2012 | Filipi et al. |
| 2013/0030351 A1 | 1/2013 | Belhe et al. |
| 2013/0079603 A1 | 3/2013 | Vargas |
| 2013/0226205 A1 | 8/2013 | Zaritsky et al. |
| 2013/0261680 A1 | 10/2013 | Baccell et al. |
| 2013/0274772 A1 * | 10/2013 | Kim ...................... A61B 17/11 606/153 |
| 2014/0058418 A1 | 2/2014 | Romley |
| 2014/0148828 A1 | 5/2014 | Ewers et al. |
| 2014/0188142 A1 | 7/2014 | Belson |
| 2014/0309634 A1 | 10/2014 | Weisshaupt et al. |
| 2014/0343576 A1 | 11/2014 | Romley |
| 2014/0350566 A1 | 11/2014 | Emmanouilidis |
| 2015/0119877 A1 | 4/2015 | Jameson et al. |
| 2015/0133771 A1 | 5/2015 | Marczyk et al. |
| 2015/0142048 A1 | 5/2015 | Coleman et al. |
| 2015/0342609 A1 | 12/2015 | DuPont et al. |
| 2017/0311952 A1 | 11/2017 | Potter et al. |
| 2017/0360524 A1 | 12/2017 | Peiro Ibanez |
| 2018/0228491 A1 | 8/2018 | Potter |

OTHER PUBLICATIONS

Harrison., "Presidential Address: What if?. . . Why not?" J Pediatric Surg., 45:1-10, 2010.

Hendren and Hale, "Electromagnetic bougienage to lengthen esophageal segments in congenital esophageal atresia," N Engl J Med, Aug. 1975, 293(9): 428-432.

Jamshidi et al., "Magnamosis: magnetic compression anastomosis with comparison to suture and staple techniques," J Pediatric Surg., 44:222-228, Jan. 2009.

Pichakron et al., "Magnamosis II: Magnetic compression anastomosis for minimally invasive gastrjejunostomy and jejunojejunostomy," J Am Coll Surg, Jan. 2011, 212(1): 42-49.

Potter, "Esophageal Atresia Repair Device," Mayo Clinic, © 2016, 1 page.

Zaritzky et al., "Magnetic compression anastomosis as a nonsurgical treatment for esophageal atresia," Pediatr Radiol, Sep. 2009, 39(9): 945-949.

* cited by examiner

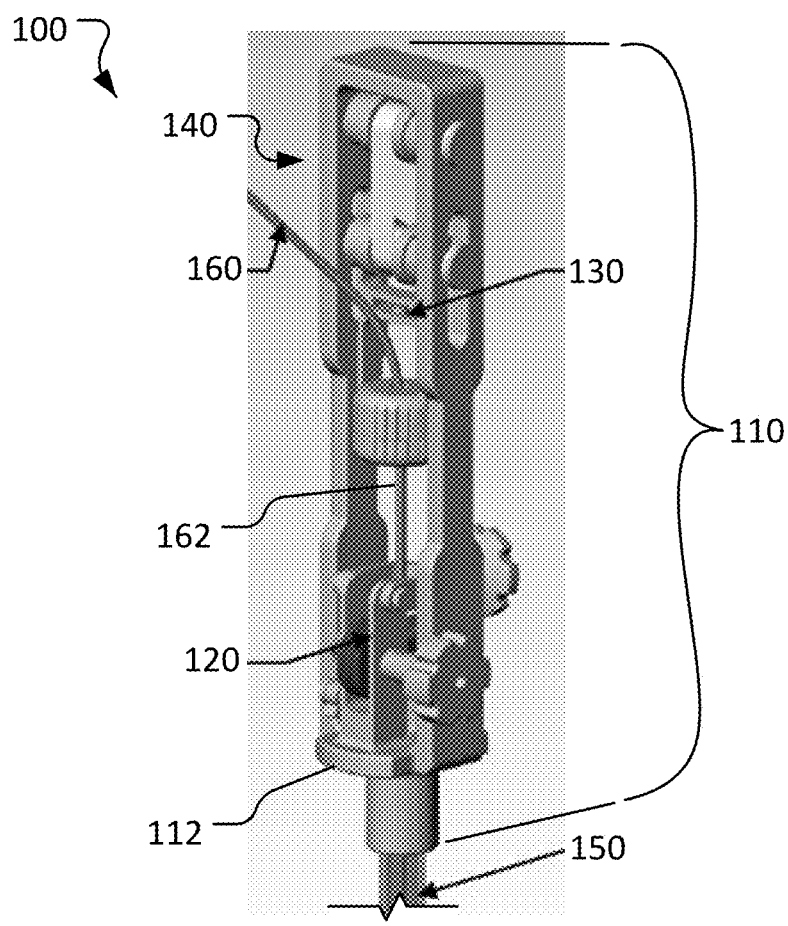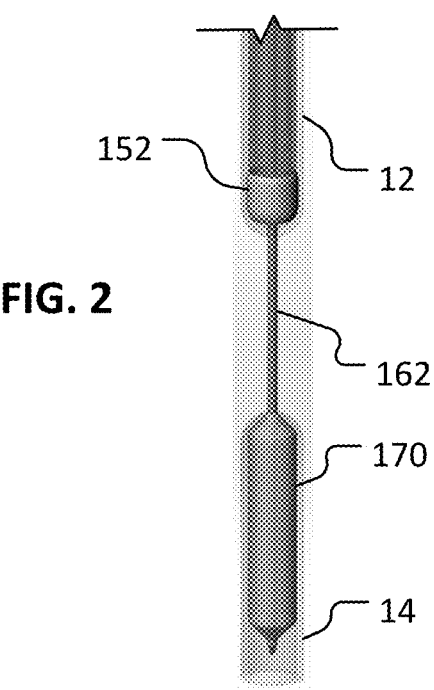
FIG. 2

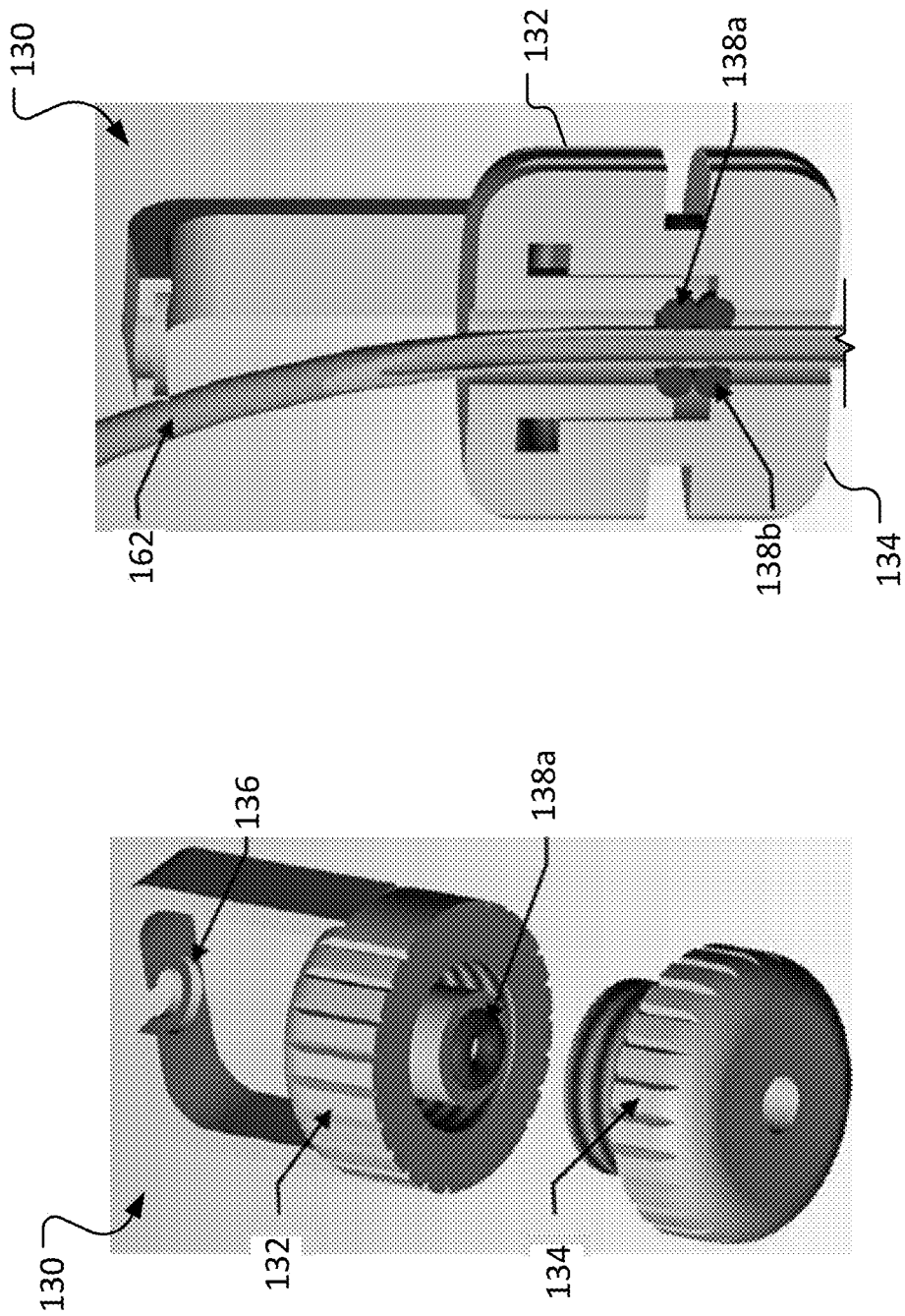

DEVICES AND METHODS FOR ESOPHAGEAL LENGTHENING AND ANASTOMOSIS FORMATION

CROSS-REFERENCE TO RELATED APPLICATIONS

This application is a divisional of U.S. application Ser. No. 15/493,947, filed Apr. 21, 2017, which claims the benefit of U.S. Provisional Application Ser. No. 62/328,970, filed Apr. 28, 2016. The disclosures of the prior application are considered part of (and are incorporated by reference in) the disclosure of this application.

BACKGROUND

1. Technical Field

This document relates to esophageal lengthening and anastomosis devices, and methods for their use. For example, this document relates to esophageal lengthening and anastomosis devices that can be used to remedy esophageal atresia in neonatal patients.

2. Background Information

Esophageal atresia (EA) is a birth defect in which the esophagus does not extend continuously into the stomach. Rather, the esophagus exists as two separate tubes; one originating from the mouth and the other ending in the stomach. It affects about one out of every 3,500 infants in the United States. The most common form of the condition is EA with a tracheoesophageal fistula (TEF) in which the lower portion of the esophagus joins with the trachea. This occurs in approximately 85% of patients. The next most common form (~10%) is pure EA in which no portion of the esophagus joins with the trachea.

Current treatment of EA with TEF, the most common form of EA, involves either a thoracotomy or minimally invasive thoracic surgery where the lower esophagus is separated from the trachea. Routinely, an anastomosis of the two esophageal ends then follows, requiring the intricate task of suturing the esophageal pouches together. The procedure has a very high success rate but is fraught with a number of complications; anastomotic leak in 10%, anastomotic stricture in 10-20%, and gastroesophageal reflux disease or severe motility dysfunction in up to 50% of patients, to name a few. These complications are believed to be caused by the tension required to re-approximate the esophageal ends for anastomosis.

Pure EA, on the other hand, cannot currently be repaired with a single procedure. That is the case because the esophagus ends are too far apart to be brought together. For example, the gap between the esophageal ends can be as long as 8 cm. Instead, typical treatment involves waiting for the esophagus to grow on its own until the ends are close together, at which point the segments can be connected. Though this process sounds reasonably straightforward, the waiting can take three to six months, and requires the infant to have a gastrostomy tube for feeding during that time. This technique is prone to the same complications mentioned above because the esophagus is, once again, under tension when repaired. Additionally, it has been shown the anastomotic leak rate and stricture formation are even higher for pure EA, due to the excessive tension required to bring the esophageal ends together.

SUMMARY

This document provides esophageal lengthening and anastomosis devices, and methods for their use. For example, this document provides esophageal lengthening and anastomosis devices that can be used to remedy esophageal atresia in neonatal patients.

In one aspect, an esophageal lengthening and anastomosis device includes: (a) a tensioning assembly including a first tensioning mechanism, a clamp, and a second tensioning mechanism (the clamp coupleable to the second tensioning mechanism); (b) a flexible sheath extending distally from the tensioning assembly and defining a sheath lumen therethrough; and (c) a catheter releasably coupleable to the first tensioning mechanism and releasably coupleable to the clamp. The catheter extends distally from the tensioning assembly through the sheath lumen. The catheter includes an inflatable balloon member at a distal end portion of the catheter. The catheter defines an inflation lumen along the catheter. The inflation lumen is in fluid communication with the balloon member. The first tensioning mechanism and the second tensioning mechanism are each configured to pull the catheter proximally in relation to the sheath.

Such an esophageal lengthening and anastomosis device may optionally include one or more of the following features. The sheath may include a distal tip and an interference fit may exist between the distal tip and the balloon member while the balloon member is inflated. A clearance fit may exist between the distal tip and the balloon member while the balloon is deflated. The tensioning assembly may include a frame to which the first tensioning mechanism and the second tensioning mechanism are each coupled. The sheath may be rigidly coupled or releasably coupleable to the frame. The first tensioning mechanism may include a tension adjustment mechanism that can be adjusted to apply a varying amount of force that pulls the catheter proximally in relation to the sheath. The first tensioning mechanism may also include a drive roller that can frictionally engage with the outer surface of the catheter in order to apply the force that pulls the catheter proximally in relation to the sheath. The second tensioning mechanism may include a spring. A second tensioning force to pull the catheter proximally in relation to the sheath can be generated by the spring. The spring may be a constant-force spring. The clamp may be releasably coupleable to the second tensioning mechanism. The clamp may be coupleable to the catheter by clamping on an outer diameter of the catheter. In some embodiments, the first tensioning mechanism can pull the catheter proximally in relation to the sheath while the second tensioning mechanism is not coupled to the catheter. In some embodiments, the second tensioning mechanism can pull the catheter proximally in relation to the sheath while the first tensioning mechanism is not coupled to the catheter. In some embodiments, the first tensioning mechanism can pull the catheter proximally in relation to the sheath while the second tensioning mechanism is not coupled to the catheter.

In another aspect, a method of treating esophageal atresia by esophageal lengthening and creating an esophageal anastomosis includes: (a) advancing a sheath defining a lumen in which a balloon catheter is slidably disposed into a first esophageal segment that extends from a mouth of a patient so that a distal end portion of the sheath abuts a terminal end of the first esophageal segment; (b) passing a distal end portion of the balloon catheter through the terminal end of the first esophageal segment; (c) passing the distal end portion of the balloon catheter through a terminal end of a second esophageal segment that extends from a stomach of the patient, wherein the distal end portion of the balloon catheter includes a balloon member; (d) inflating the balloon member while the balloon member is residing in the second esophageal segment; and (e) exerting a first tension on the balloon catheter in relation to the sheath so that the terminal end of the first esophageal segment and the terminal end of the second esophageal segment are drawn closer to each other.

Such a method of treating esophageal atresia by esophageal lengthening and creating an esophageal anastomosis may optionally include one or more of the following features. The method may further comprise allowing a first period of time to pass while the first tension is being exerted, then adjusting the first tensioning mechanism to apply a second tension on the balloon catheter in relation to the sheath. The second tension may draw the terminal end of the first esophageal segment and the terminal end of the second esophageal segment closer to each other than the first tension did. The method may further comprise allowing a second period of time to pass while the second tension is being exerted, then engaging a second tensioning mechanism with the balloon catheter and disengaging the first tensioning mechanism from the balloon catheter, wherein the second tensioning mechanism is coupled to the sheath. The method may further comprise exerting, using the second tensioning mechanism, a third tension on the balloon catheter in relation to the sheath. The second tensioning mechanism may comprise a constant-force spring for exerting the third tension. The terminal end of the first esophageal segment and the terminal end of the second esophageal segment may be in contact with each other while the third tension is being exerted. The method may further comprise allowing a third period of time to pass while the third tension is being exerted. In some embodiments, after the third period of time an anastomosis is created between the first esophageal segment and the second esophageal segment.

In another aspect, an esophageal lengthening and anastomosis device includes: (i) a tensioning assembly including a tensioning mechanism and a clamp that is coupleable to the tensioning mechanism; (ii) a flexible sheath extending distally from the tensioning assembly and defining a sheath lumen therethrough; and (iii) a catheter releasably coupleable to the tensioning mechanism and releasably coupleable to the clamp. The catheter extends distally from the tensioning assembly through the sheath lumen. The catheter includes an inflatable balloon member at a distal end portion of the catheter. The catheter defines an inflation lumen along the catheter. The inflation lumen is in fluid communication with the balloon member. The tensioning mechanism is configured to pull the catheter proximally in relation to the sheath.

Such an esophageal lengthening and anastomosis device may optionally include one or more of the following features. The sheath may include a distal tip and an interference fit may exist between the distal tip and the balloon member while the balloon member is inflated. A clearance fit may exist between the distal tip and the balloon member while the balloon is deflated. The tensioning assembly may include a frame to which the tensioning mechanism is coupled. The sheath may be rigidly coupled or releasably coupleable to the frame. The tensioning mechanism may include a tension adjustment mechanism that can be adjusted to apply a varying amount of force that pulls the catheter proximally in relation to the sheath. The tensioning mechanism may include a spring, and a tensioning force to pull the catheter proximally in relation to the sheath may be generated by the spring. In some embodiments, the spring may be a constant-force spring. In some embodiments, the clamp may be releasably coupleable to the tensioning mechanism. In some embodiments, the clamp may be coupleable to the catheter by clamping on an outer diameter of the catheter.

Particular embodiments of the subject matter described in this document can be implemented to realize one or more of the following advantages. First, only one operation is required to place the device and connect the esophageal ends, whereas previous technique requires at a minimum two operations. Second, by inducing growth of the esophageal ends by tension, the number of anastomotic leaks and strictures will likely decrease. Third, the length of hospitalization, the potential for trauma and complications, and cost of care of these complex patients will likely be reduced. Fourth, in the case of pure EA, the prolonged treatment time of three to six months for the conventional technique brings with it abundant hurdles to overcome. These infants require suctioning of the saliva that accumulates in the upper esophageal pouch. Despite this removal, many of the infants still develop chronic lung disease as a result of the aspiration of their own saliva. Additionally, these children have never consumed nutrition by mouth due to the esophageal obstruction, thus they develop oral aversion. This problem does resolve; however, retraining to eat can take years. Though one could wait longer for the esophagus to grow such that no tension is present when it is connected, it is critical that the esophagus be connected as soon as possible to hopefully lessen the severity of chronic lung disease and oral aversion. To that end, the devices and methods provided herein can reduce the treatment time to several weeks in infants with pure EA.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 2 is a perspective view of an example esophageal lengthening and anastomosis device in accordance with some embodiments provided herein.

FIG. 4 is an exploded perspective view of a catheter clamp component of the esophageal lengthening and anastomosis device of FIG. 2.

FIG. 5 is a longitudinal cross-sectional view of the catheter clamp component of FIG. 4.

Like reference numbers represent corresponding parts throughout.

DETAILED DESCRIPTION

This disclosure provides devices and methods to treat long gap EA, while obviating much of the delay and complexities associated with current procedures. The devices and methods provided herein involve actively stretching the esophagus portions with traction to promote growth of the esophagus portions. Moreover, the devices and methods provided herein allow for a compression anastomosis to occur between the esophageal ends. This eliminates the need for a second operation to suture the esophageal ends together.

The anastomotic devices provided herein use an oroesophageal tube that is passed through the baby's mouth to apply pressure on the upper esophageal segment. A balloon tipped catheter is passed via the tube through the upper esophageal segment and into the lower esophageal segment. Once the balloon is inflated and secured, traction is applied between the esophageal ends over a period of several days. Once the esophageal ends have grown together, the balloon and oroesophageal tube will unite to create a compression anastomosis between the two esophageal ends. After formation of the tissue anastomosis, the device would then be ready to slip out of the patient's mouth.

In this context, compression anastomosis involves connecting two bowel segments by axially compressing the two ends together and holding them in place to create an internal tissue-growth connection. That is, the two ends will fuse together creating a natural anastomosis while the superfluous flesh loses blood supply and auto-amputates.

Figure 1:
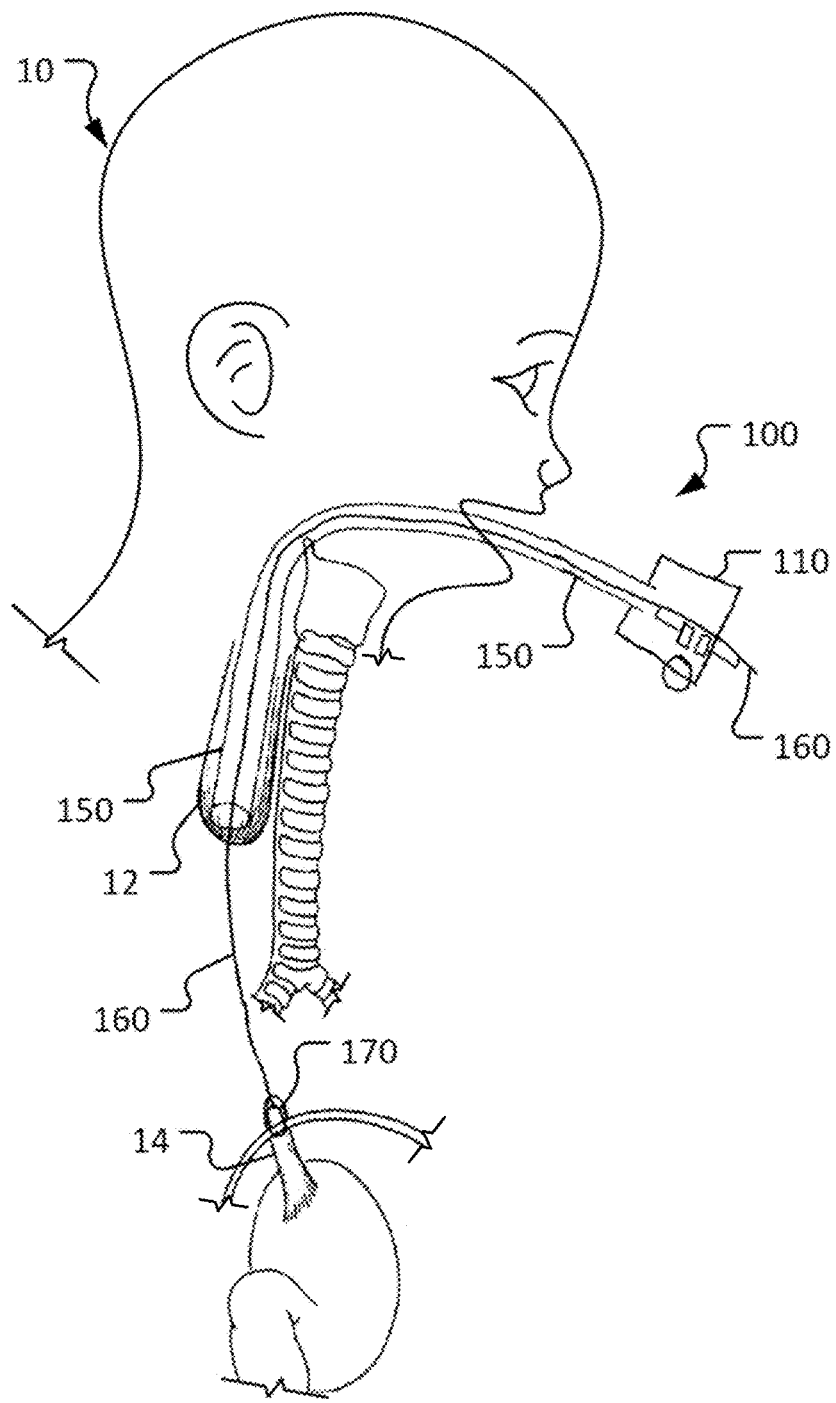
FIG. 1 is a schematic diagram of patient undergoing an esophageal lengthening treatment using an esophageal lengthening and anastomosis device in accordance with some embodiments provided herein.

Referring to FIG. 1, an infant patient 10 is receiving treatment for EA using an example esophageal lengthening and anastomosis device 100. The treatment includes the application of traction between: (a) a first esophageal segment 12 that extends from the mouth of patient 10 and (b) a second esophageal segment 14 that extends from the stomach of the patient 10. As described further below, the traction force is exerted by esophageal lengthening and anastomosis device 100.

Over time, the traction force exerted by esophageal lengthening and anastomosis device 100 will cause the terminal ends of first esophageal segment 12 and second esophageal segment 14 to become closer together. At one or more occasions during that time, a clinician may adjust esophageal lengthening and anastomosis device 100 to continue the exertion of a desired level of traction force as the terminal ends of first esophageal segment 12 and second esophageal segment 14 become closer together.

Eventually, the terminal ends of first esophageal segment 12 and second esophageal segment 14 will reach each other, and will become approximated with each other. At that stage of the treatment, as described further below, esophageal lengthening and anastomosis device 100 will help cause the creation of a compression anastomosis between first esophageal segment 12 and second esophageal segment 14. After formation of the anastomosis, the esophagus of patient 10 will be a patent conduit extending from the mouth to the stomach, which is the intended result of the treatment. Hence, esophageal lengthening and anastomosis device 100 facilitates: (i) lengthening of the esophageal segments 12 and 14, and (ii) the creation of a tissue anastomosis between the esophageal segments 12 and 14.

Example esophageal lengthening and anastomosis device 100 includes a tensioning assembly 110, a flexible sheath 150, a catheter 160, and an inflatable balloon member 170. Flexible sheath 150 extends distally from tensioning assembly 110. In some embodiments, flexible sheath 150 is rigidly coupled to tensioning assembly 110. In some embodiments, flexible sheath 150 is releasably coupled to tensioning assembly 110. Flexible sheath 150 defines a lumen extending longitudinally along the length of flexible sheath 150. Catheter 160 extends distally from tensioning assembly 110 and passes through the lumen of flexible sheath 150. As described further below, catheter 160 is releasably coupleable to one or more portions of tensioning assembly 110. Inflatable balloon member 170 is coupled to a distal end portion of catheter 160. Inflatable balloon member 170 is expandable and retractable in response to the supply of an inflation fluid and the withdrawal of the inflation fluid respectively. Catheter 160 includes an inflation fluid lumen along a length of catheter 160. The inflation fluid lumen is in fluid communication with inflatable balloon member 170.

The esophageal lengthening and anastomosis device 100 may be put into the depicted operative arrangement in relation to patient 10 using various suitable medical techniques. For example, thoracoscopic and/or endoscopic surgical techniques are used in some cases. Moreover, imaging techniques such as fluoroscopy and/or ultrasound are used in some cases.

While balloon member 170 is in its deflated configuration, the distal end portion of catheter 160 is passed through the terminal ends of both esophageal segments 12 and 14. Thereafter, while inflatable balloon member 170 is within second esophageal segment 14, inflatable balloon member 170 is inflated. In some cases, reinforcement (e.g., one or more sutures, clips, pledgets, etc.) may be added to the terminal end of second esophageal segment 14.

In the depicted operative arrangement, a distal end portion of sheath 150 abuts the terminal end of first esophageal segment 12, and inflatable balloon member 170 (in its inflated configuration) abuts the terminal end of second esophageal segment 14. Tensioning assembly 110 can then be used to pull catheter 160 proximally, while maintaining the position of sheath 150 stationary (in relation to tensioning assembly 110). Accordingly, as a result of the traction force, the terminal ends of first esophageal segment 12 and second esophageal segment 14 will be drawn closer together along the axis of catheter 160. Over a period of time, esophageal segments 12 and 14 will become lengthened. During that time, the traction force exerted by tensioning assembly 110 (and sheath 150 and balloon member 170) can be adjusted one or more times. Such adjustments involve changing the relative position of catheter 160 with respect to tensioning assembly 110. That is, to add traction force, the catheter 160 is moved proximally in relation to tensioning assembly 110. As described further below, tensioning assembly 110 has one or more mechanism for facilitating such relative movements/adjustments.

Referring also to FIG. 2, a first example embodiment of esophageal lengthening and anastomosis device 100 is depicted in greater detail. In the depicted embodiment, esophageal lengthening and anastomosis device 100 includes tensioning assembly 110, flexible sheath 150, catheter 160, and inflatable balloon member 170. Additional design embodiments of esophageal lengthening and anastomosis device 100 are described below.

Flexible sheath 150 can be a tubular member such as a nasogastric (NG) tube and the like, for example. Flexible sheath 150 can be made from any suitable material such as, but not limited to, PEBEX, PICOFLEX, PTFE, ePTFE, FEP, PEEK, silicone, PVC, urethane, polyethylene, polypropylene, and the like, and combinations thereof.

In some embodiments, flexible sheath 150 includes an adjunct end cap member 152 at the distal end of flexible sheath 150. In some embodiments, end cap member 152 makes the distal tip of flexible sheath 150 more atraumatic (e.g., so that sheath 150 does not puncture through the terminal end of first esophageal segment 12). Additionally, end cap member 152 can be configured with a design that is complementary with inflatable balloon member 170 for creation of a compression anastomosis. In some embodiments, end cap member 152 includes one or more radiopaque (RO) markers.

Catheter 160 includes a catheter shaft 162. Catheter shaft 162 can be made from any suitable material such as, but not limited to, PEBEX, PICOFLEX, PTFE, ePTFE, FEP, PEEK, silicone, PVC, urethane, polyethylene, polypropylene, and the like, and combinations thereof. Catheter shaft 162 defines an inflation lumen for conveyance of inflation media to inflatable balloon member 170. In some embodiments, catheter shaft 162 also defines another lumen for slidably receiving a guidewire. That is, in some embodiments catheter 160 can be configured for deployment using an over-the-wire or a rail technique using a guidewire. In some embodiments, the distal tip of catheter shaft 162 extends distally beyond inflatable balloon member 170. In some such cases, the distal tip of catheter shaft 162 is configured for piercing tissue (e.g., with a pointed or beveled tip). Catheter shaft 162 may include one or more RO markers at various locations.

Inflatable balloon member 170 is coupled to a distal end portion of catheter shaft 162. In some embodiments, inflatable balloon member 170 is a high-pressure, non-elastic dilatation or angioplasty-type balloon (e.g., made of nylon, PET, PVC, PE, polyurethane, and the like). In some embodiments, inflatable balloon member 170 is a low-pressure, elastomeric balloon (e.g., made of latex, silicone, and the like). Inflatable balloon member 170 can have various shapes. For example inflatable balloon member 170 can be cylindrical (as shown), spherical, square, tapered, stepped, dog bone, offset, and the like. One or more of the ends of inflatable balloon member 170 can be conical (as shown), radiused, square, spherical, and the like. Inflatable balloon member 170 may include one or more RO markers at various locations.

In the depicted embodiment, tensioning assembly 110 includes a frame 112, a first tensioning mechanism 120, a clamp 130, and a second tensioning mechanism 140. In some embodiments, a single tensioning mechanism is included, and a clamp may or may not be included. The primary function of tensioning assembly 110 is to provide an adjustable application of tension (pull in the proximal direction) on catheter shaft 162 while maintaining sheath 150 stationary. First tensioning mechanism 120 is coupled to frame 112. Clamp 130 is releasably coupleable with second tensioning mechanism 140. Second tensioning mechanism 140 is coupled to frame 112. Catheter shaft 162 is releasably coupleable with first tensioning mechanism 120, and releasably coupleable with clamp 130.

Figure 3:
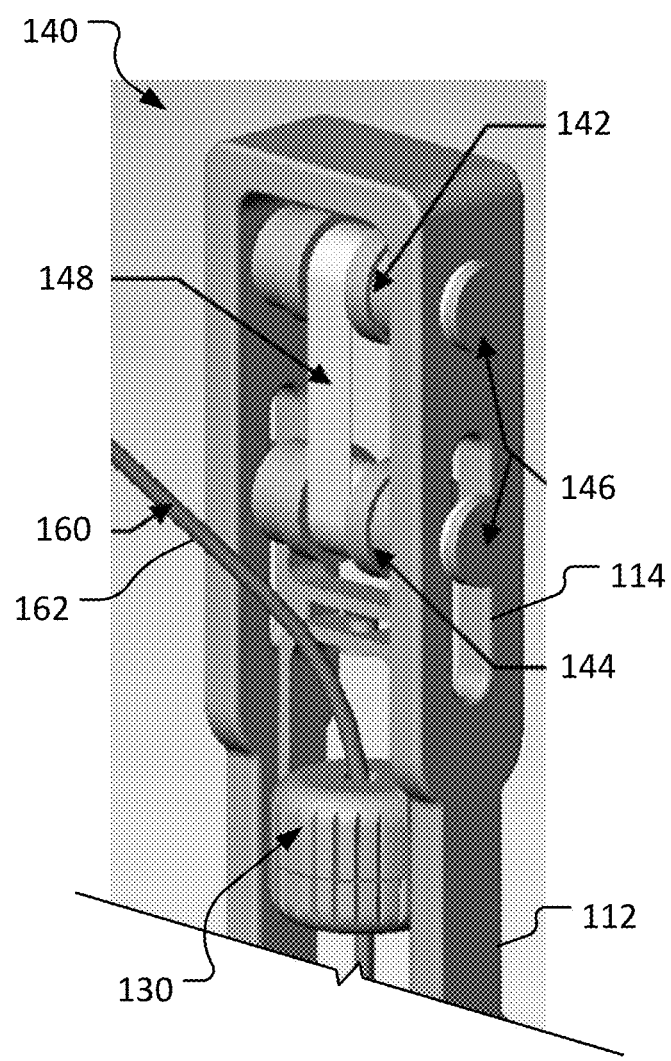
FIG. 3 is a perspective view of the proximal end portion of the esophageal lengthening and anastomosis device of FIG. 2.

Referring to FIG. 3, second tensioning mechanism 140 is shown in greater detail. In some embodiments, second tensioning mechanism 140 is the sole tensioning mechanism included in an esophageal lengthening and anastomosis device. That is, in some embodiments second tensioning mechanism 140 provides the tension to catheter shaft 162 for both treatment steps: (i) lengthening of the esophageal segments, and (ii) the creation of a tissue anastomosis between the esophageal segments). In some embodiments, second tensioning mechanism 140 is one of two different tensioning mechanisms included in an esophageal lengthening and anastomosis device (e.g., as shown in FIG. 2).

In the depicted embodiment, second tensioning mechanism 140 is coupled to frame 112 and releasably coupleable with clamp 130 (to which catheter 160 is releasably and adjustably coupled). Second tensioning mechanism 140 can apply a tension to catheter 160 via clamp 130.

In the depicted embodiment, second tensioning mechanism 140 includes a spinning spool 142, a sliding spool 144, two spool pins 146, and a spring 148. Spinning spool 142 is rotatably coupled with frame 112 via spool pin 146. Sliding spool 144 is slidably coupled with frame 112 via spool pin 146 that is engaged with a slot 114 defined by frame 112. One or more low-friction washers or bushings may be included such that spools 142 and 144 are free to move in relation to frame 112 as desired. Spring 148 extends between spinning spool 142 and sliding spool 144. That is, spring 148 is biased to draw sliding spool 144 proximally towards spinning spool 142. In doing so, spring 148 coils onto spinning spool 142.

In some embodiments (such as the depicted embodiment), spring 148 is a constant-force spring. While not required for all embodiments, a constant-force spring may be advantageous for applying a consistent tension on catheter 160 during the formation of the compression anastomosis. Hence, second tensioning mechanism 140 can be particularly useful for the anastomosis formation portion of the EA treatment method provided herein.

Referring also to FIGS. 4 and 5, an example embodiment of clamp 130 is shown in greater detail. Clamp 130 is configured and operable for releasably coupling with catheter shaft 162 and with second tensioning mechanism 140. Clamp 130 includes a first clamp portion 132, a second clamp portion 134, a mounting feature 136 and clamp members 138a/138b. In the depicted embodiment, clamp portions 132 and 134 are threadably coupleable with each other. Catheter shaft 162 can pass through openings in each of clamp portions 132 and 134. Other coupling configurations can readily be incorporated.

Mounting feature 136 is used for releasably coupling clamp 130 to second tensioning mechanism 140. In the depicted embodiment, mounting feature 136 is a keyhole that can engage with a mushroom head pin of second tensioning mechanism 140. Other coupling configurations can readily be incorporated.

In the depicted embodiment, clamp members 138a/138b are compressible members disposed between clamp portions 132 and 134. For example, clamp members 138a/138b can be one or more resilient polymer O-rings. Clamp members 138a/138b are compressed between clamp portions 132 and 134, while catheter shaft 162 is passed through openings in clamp members 138a/138b. In result, compression of clamp portions 132 and 134 deforms clamp members 138a/138b such that clamp members 138a/138b frictionally engage with the outer surface of catheter shaft 162. Hence, by tightening clamp portions 132 and 134 together, the holding power of clamp 130 on catheter shaft 162 is increased. Other configurations for coupling clamp 130 and catheter shaft 162 can readily be incorporated.

Other design embodiments of clamp 130 are also envisioned within the scope of this disclosure. For example, catheter 160 may be clamped by threading catheter shaft 162 through a series of posts or projections in a serpentine fashion. Tapered locking mechanisms, collet devices, clamp devices, ratchet devices, and the like can be used as part of clamp 130 for catheter shaft 162 to the tensioning mechanisms provided herein.

Figure 7:
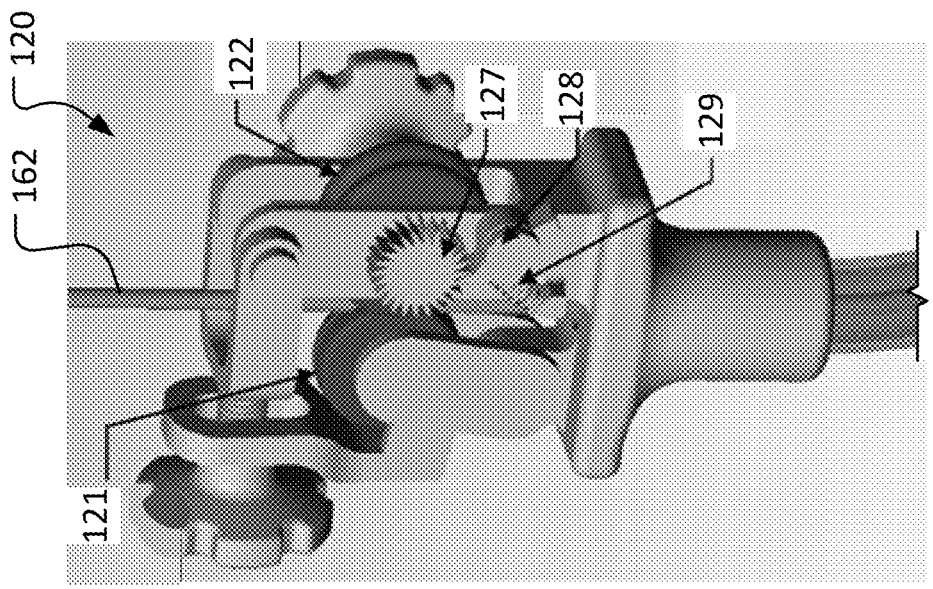
FIGS. 6 and 7 are perspective views of another portion of the esophageal lengthening and anastomosis device of FIG. 2.
Figure 6:
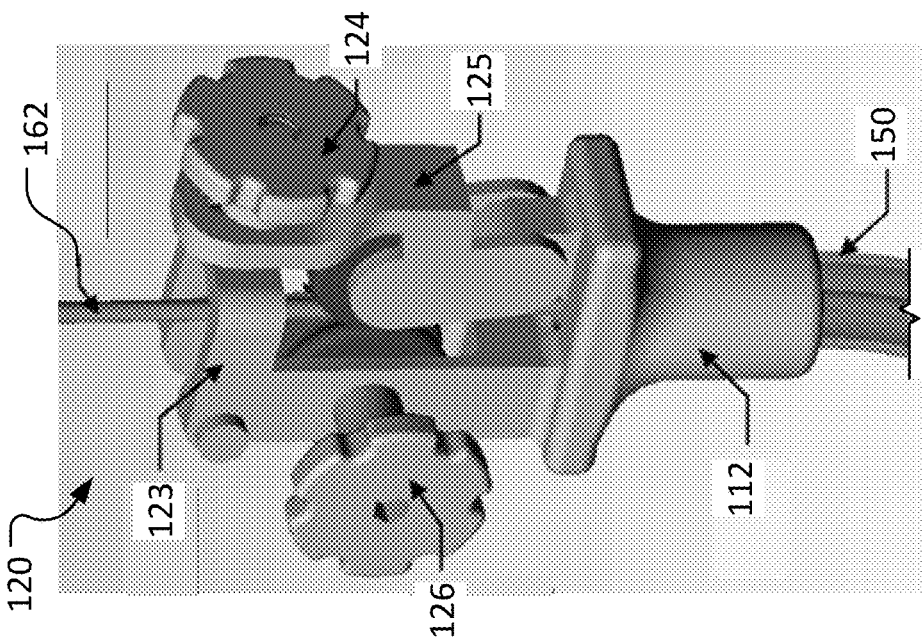

Referring to FIGS. 6 and 7, first tensioning mechanism 120 is shown in greater detail. In some embodiments, first tensioning mechanism 120 is the sole tensioning mechanism included in an esophageal lengthening and anastomosis device. In some embodiments, first tensioning mechanism 120 is one of two different tensioning mechanisms included in an esophageal lengthening and anastomosis device (e.g., as shown in FIG. 2). As depicted in FIG. 2, in some embodiments, first tensioning mechanism 120 is located distally of second tensioning mechanism 140.

In the depicted embodiment, first tensioning mechanism 120 is coupled to frame 112 and releasably/adjustably coupled with catheter shaft 162. First tensioning mechanism 120 includes a clamping roller 121, a drive roller 122, a clamping yoke 123, a clamping knob 124, a clamping bracket 125, a tension adjustment knob 126, a ratchet gear 127, a ratchet pawl 128, and a ratchet spring 129. Clamping roller 121 and drive roller 122 are configured to frictionally engage with each other and with the outer surface of catheter shaft 162 therebetween. Hence, in some embodiments clamping roller 121 and drive roller 122 are made of a material with a high coefficient of friction in relation to catheter shaft 162. Such materials can include, but are not limited to, neoprene, silicone, and the like.

Clamping roller 121 and drive roller 122 are rotatably coupled to clamping bracket 125 and frame 112 respectively. The compression between clamping roller 121 and drive roller 122 is user-adjustable. Compression between clamping roller 121 and drive roller 122 can be adjusted by turning clamping knob 124. Since clamping bracket 125 is coupled with clamping roller 121 and pivotably coupled to frame 112, as clamping knob 124 is turned, clamping roller 121 will be moved toward or away from drive roller 122.

Tension on catheter shaft 162 can be user-adjusted by rotating tension adjustment knob 126, which is coupled with drive roller 122 and ratchet gear 127. In some embodiments, a slip clutch is included as part of tension adjustment knob 126 so that excessive tensioning of catheter shaft 162 is prevented/avoidable. The applied tension on catheter shaft 162 can be maintained by virtue of ratchet gear 127 that is engaged with ratchet pawl 128 and ratchet spring 129 in a conventional ratcheting mechanism arrangement.

Referring again to FIG. 2, in some cases first tensioning mechanism 120 can be particularly well-suited for applying tension to catheter shaft 162 for elongating the esophageal segments. Hence, in some cases, during the esophageal segment elongation process, the user will disengage second tensioning mechanism 140 from catheter shaft 162 and let the first tensioning mechanism 120 provide the sole means of tensioning catheter shaft 162. When the esophageal segments are elongated to the extent that their terminal ends are approximate with each other, then the compression anastomosis process can begin. In some cases, second tensioning mechanism 140 can be particularly well-suited for applying tension to catheter shaft 162 during the compression anastomosis formation process. Hence, in some cases, during the compression anastomosis formation process, the user will disengage first tensioning mechanism 120 from catheter shaft 162 and let the second tensioning mechanism 140 provide the sole means of tensioning catheter shaft 162.

In some embodiments, to facilitate the compression anastomosis formation process, an interference fit exists between the outer diameter of the inflatable balloon member 170 (while in its inflated configuration) and an inner diameter of end cap member 152. Alternatively, in some embodiments to facilitate the compression anastomosis formation process, a clearance fit or a line-to-line fit exists between the outer diameter of the inflatable balloon member 170 (while in its inflated configuration) and an inner diameter of end cap member 152.

Figure 8:
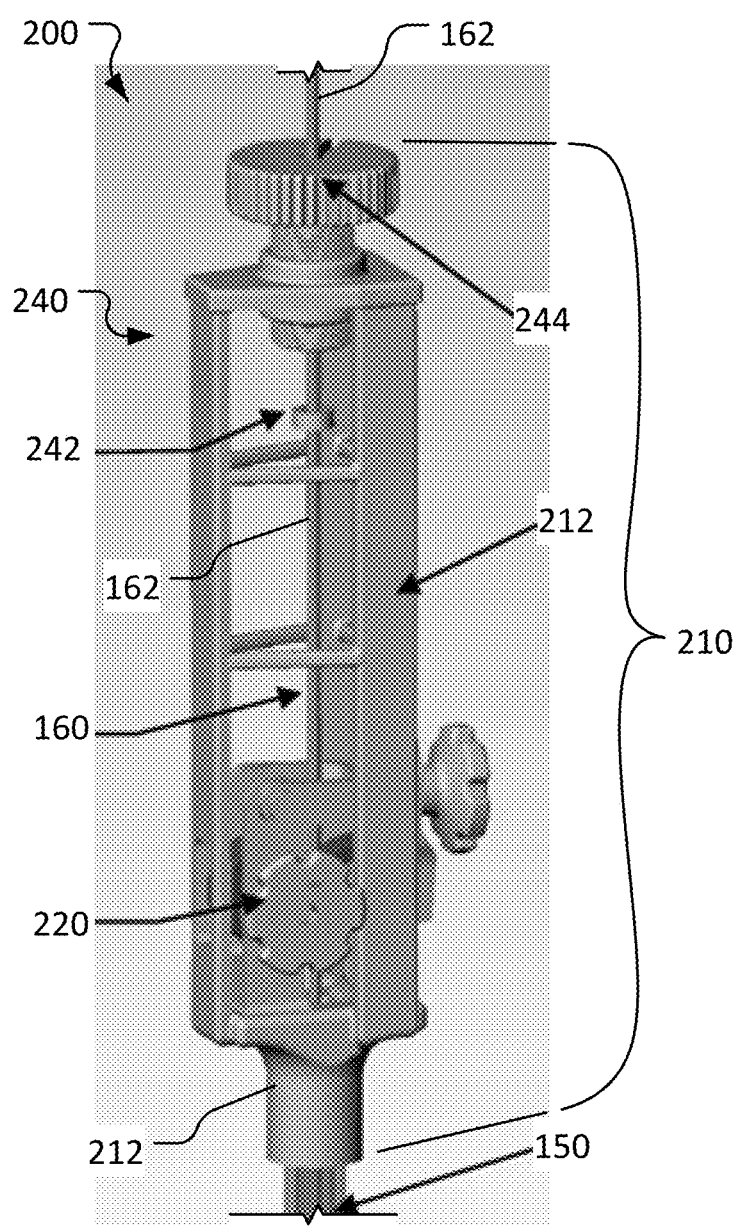
FIG. 8 is a perspective view of a proximal end portion of another example esophageal lengthening and anastomosis device in accordance with some embodiments provided herein.

Referring to FIG. 8, another example esophageal lengthening and anastomosis device 200 is provided. Esophageal lengthening and anastomosis device 200 can be clinically used to treat EA in a similar way to esophageal lengthening and anastomosis device 100 as described above. That is, esophageal lengthening and anastomosis device 200 can be used to lengthen esophageal segments and to subsequently facilitate a compression anastomosis between the terminal ends of the esophageal segments.

Esophageal lengthening and anastomosis device 200 includes a tensioning assembly 210, a flexible sheath 150, a catheter 160, and an inflatable balloon member 170 (not shown in FIG. 8; refer to FIG. 2). Flexible sheath 150, catheter 160, and inflatable balloon member 170 can be the same as described above in the context of esophageal lengthening and anastomosis device 100.

Tensioning assembly 210 includes a first tensioning mechanism 220 and a second tensioning mechanism 240. First tensioning mechanism 220 can be analogous to first tensioning mechanism 120 as described above in the context of esophageal lengthening and anastomosis device 100.

Second tensioning mechanism 240 is physically different than second tensioning mechanism 140 described above. In the depicted embodiment, second tensioning mechanism 240 includes a catheter magnet 242 and an upper magnet screw 244 (which may also contain a magnet, not shown). Catheter magnet 242 is fixedly coupled to catheter shaft 162. Upper magnet screw 244 is adjustably coupled with frame 212. That is, upper magnet screw 244 can be adjusted proximally and distally in relation to frame 212. In the depicted embodiment, upper magnet screw 244 is threadably engaged with frame 212 to facilitate the adjustments.

In some embodiments, catheter magnet 242 is a neodymium-iron-boron magnet. In some embodiments, a magnet within upper magnet screw 244 is also a neodymium-iron-boron magnet. When catheter magnet 242 is magnetically coupled with upper magnet screw 244 a constant-force tension is applied to catheter shaft 162.

In some cases, first tensioning mechanism 220 can be particularly well-suited for applying tension to catheter shaft 162 for elongating the esophageal segments. Hence, in some cases, during the esophageal segment elongation process, the user will disengage second tensioning mechanism 240 from catheter shaft 162 and let the first tensioning mechanism 220 provide the sole means of tensioning catheter shaft 162. When the esophageal segments are elongated to the extent that their terminal ends are approximate with each other, then the compression anastomosis process can begin. In some cases, second tensioning mechanism 240 can be particularly well-suited for applying tension to catheter shaft 162 during the compression anastomosis formation process. Hence, in some cases, during the compression anastomosis formation process, the user will disengage first tensioning mechanism 220 from catheter shaft 162 and let the second tensioning mechanism 240 provide the sole means of tensioning catheter shaft 162.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of treating esophageal atresia by esophageal lengthening and creating an esophageal anastomosis, the method comprising:
    advancing a sheath defining a lumen in which a balloon catheter is slidably disposed into a first esophageal segment that extends from a mouth of a patient so that a distal end portion of the sheath abuts a terminal end of the first esophageal segment;
    passing a distal end portion of the balloon catheter through the terminal end of the first esophageal segment;
    passing the distal end portion of the balloon catheter through a terminal end of a second esophageal segment that extends from a stomach of the patient, wherein the distal end portion of the balloon catheter includes a balloon member;
    inflating the balloon member while the balloon member is residing in the second esophageal segment; and
    exerting a first tension on the balloon catheter in relation to the sheath so that the terminal end of the first esophageal segment and the terminal end of the second esophageal segment are drawn closer to each other,
    wherein the balloon catheter is coupled to a sliding mechanism of a tensioning assembly,
    wherein the tensioning assembly also includes a tensioning mechanism and a frame, and
    wherein the first tension is generated by the tensioning mechanism as the tensioning mechanism provides motive force to cause the sliding mechanism to translate along the frame.

2. The method of claim 1, wherein the sheath is fixed to the frame.

3. The method of claim 2, further comprising allowing a first period of time to pass while the first tension is being exerted, then adjusting the tensioning assembly to apply a second tension on the balloon catheter in relation to the sheath, wherein the second tension draws the terminal end of the first esophageal segment and the terminal end of the second esophageal segment closer to each other than the first tension did.

4. The method of claim 2, wherein the sliding mechanism is proximally and distally translatable in relation to the frame, and
    wherein the tensioning mechanism is coupled to the frame and the sliding mechanism.

5. The method of claim 1, wherein the tensioning assembly resides externally of the patient while the method is performed.

6. The method of claim 1, wherein the method causes lengthening of one or both of the first esophageal segment and the second esophageal segment.

7. The method of claim 6, wherein, as a result of the lengthening, the terminal end of the first esophageal segment and the terminal end of the second esophageal segment contact each other.

8. The method of claim 7, further comprising creating an anastomosis between the terminal end of the first esophageal segment and the terminal end of the second esophageal segment.

9. The method of claim 8, wherein the anastomosis creates a patent conduit extending from the mouth of the patient to the stomach of the patient that includes the first esophageal segment and the second esophageal segment.

10. The method of claim 8, wherein the distal end portion of the sheath defines an inner diameter that is smaller than an outer diameter of the balloon member while the balloon member is inflated.

11. The method of claim 8, wherein the distal end portion of the sheath defines an inner diameter that is larger than an outer diameter of the balloon member while the balloon member is inflated.

12. A method of treating esophageal atresia by esophageal lengthening and creating an esophageal anastomosis, the method comprising:
    advancing a sheath defining a lumen in which a catheter is slidably disposed into a first esophageal segment that extends from a mouth of a patient so that a distal end of the sheath abuts and applies pressure against a terminal end of the first esophageal segment;
    passing a distal end portion of the catheter through the terminal end of the first esophageal segment;
    passing the distal end portion of the catheter through a terminal end of a second esophageal segment that extends from a stomach of the patient; and
    exerting a first tension on the catheter in relation to the sheath so that the terminal end of the first esophageal segment and the terminal end of the second esophageal segment are drawn closer to each other.

13. The method of claim 12, wherein the distal end portion of the catheter includes an expandable member.

14. The method of claim 13, wherein the expandable member is a balloon.

15. The method of claim 13, further comprising expanding the expandable member after the distal end portion of the catheter is passed through the terminal ends of the first and second esophageal segments.

\* \* \* \* \*

UNITED STATES PATENT AND TRADEMARK OFFICE
CERTIFICATE OF CORRECTION

PATENT NO. : 11,006,958 B2
APPLICATION NO. : 16/382711
DATED : May 18, 2021
INVENTOR(S) : D. Dean Potter, Jr.

It is certified that error appears in the above-identified patent and that said Letters Patent is hereby corrected as shown below:

In the Claims

In Column 12, Line 38, In Claim 9, delete "patent" and insert -- patient --, therefor.

Signed and Sealed this
Twenty-ninth Day of October, 2024

Katherine Kelly Vidal
*Director of the United States Patent and Trademark Office*